United States Patent [19]

Kaminski

[11] Patent Number: 5,177,081
[45] Date of Patent: Jan. 5, 1993

[54] METHOD AND PHARMACEUTICAL COMPOSITION FOR THE TREATMENT OF SCHIZOPHRENIA

[75] Inventor: Ram Kaminski, Riverdale, N.Y.

[73] Assignee: The Mount Sinai School of Medicine of the City University of New York, New York, N.Y.

[21] Appl. No.: 743,254

[22] Filed: Aug. 9, 1991

Related U.S. Application Data

[62] Division of Ser. No. 655,759, Feb. 14, 1991, Pat. No. 5,070,101.

[51] Int. Cl.$^5$ .............. A61K 31/34; A61K 31/44; A61K 31/415
[52] U.S. Cl. .................. 514/279; 514/399; 514/471
[58] Field of Search .............. 514/279, 399, 471

[56] References Cited

PUBLICATIONS

Chem. Abst. 103-52159y (1985).
Chem. Abst. 110-107925x (1989).
Chem. Abst. 104-28834q (1986).
Kaminski et al., Effect of famotidine on deficit symptoms of schizophrenia The Lancet, (1990) vol. 335, pp. 1351-1352.
Pickar et al., Neurochemical and Neural Mechanisms . . . Mod. Probl. Pharmacopsychiatry. Basel, (1990) vol. 24. pp. 124-151.
Morrison et al., Positive and Negative Symptoms in Schizophrenia The Journal of Nervous and Mental Disease, (1990) vol. 178, No. 6 pp. 377-384.
Carpenter et al., Deficit and Nondeficit Forms of Schizophrenia . . . Am. J. Psychiatry, (1988) vol. 145, No. 5 pp. 578-583.
Wyatt et al, Schizophrenia, just the facts . . . Schizophrenia Research, (1988) vol. 1 pp. 3-18.
Mesulam, Schizophrenia and the Brain The New England Journal of Medicine, (1990) vol. 322, No. 12 pp. 842-844.
Schwartz et al., Properties and Roles of the Three Subclasses of Histamine . . . J. exp. Biol., printed in Great Britain, (1986) vol. 124, pp. 203-224.
Itoh et al., Effects of Nociceptive Stimuli on Brain Histamine Dynamics Japan, J. Pharmacol. (1989) vol. 49, pp. 449-454.
Gogas et al., Inhibition of Naloxone-Resistant Antinociception . . . The Journal of Pharmacology and Experimental Therapeutics, (1989) vol. 248, No. 1.
Hough et al., A Role for Histamine and Histamine $H_2$-Receptors . . . Life Sciences, (1985) vol. 36, pp. 859-866.
Prell, Ann. Rev. Neurosci (1986) vol. 9, pp. 209-254.
Heleniak et al., Histamine Methylation in Schizophrenia Medical Hypotheses, (1989) vol. 30, pp. 167-174.
Heleniak et al., Histamine and Prostaglandins in Schizophrenia Journal of Orthomolecular Psychiatry, vol. 14, No. 3, pp. 162-177.
Lucca et al., Biochemical Investigation of Histidinemia . . . Bil. Psychiatry, (1990) vol. 27, pp. 69-75.
Hough, Cellular Localization and Possible Functions for Brain Histamine . . . Progress in Neurobiology, (1988) vol. 30, pp. 469-505.
White et al., Behavioural effects of histamine and its antagonists: a review Psychopharmacology, (1988) vol. 95, pp. 1-14.
Emsley et al., Water Excretion and Plasma Vasopressin in Psychotic Disorders Am. J. Psychiatry (1989) vol. 146, No. 2, pp. 250-253.
Specht et al., Histamine-Elicted Drinking in Weanling and Adult Rats Physiology & Behavior, (1989) vol. 45, pp. 63-70.
Koczapski et al., Individual Differences in Serum Sodium Level . . . Am. J. Psychiatry, (1989) vol. 146, No. 12 pp. 1614-1615.
USP DI, (1990) Histamine $H_2$-Receptor Antagonists (systemic) pp. 11496-1505.
Gelenberg, Famotidine for Schizophrenia?—Biological Therapies in Psychiatry (Newsletter) (1990) vol. 13, No. 11 pp. 41 and 44.

*Primary Examiner*—S. J. Friedman
*Attorney, Agent, or Firm*—Brumbaugh, Graves, Donohue & Raymond

[57] ABSTRACT

Persons suffering from negative symptoms of schizophrenia can be successfully treated using a histamine $H_2$-antagonist which crosses the blood-brain barrier so as to interact with histamine-$H_2$ receptors in the brain. A preferred $H_2$-antagonist is famotidine. The $H_2$-antagonist may be used alone in patients who are relatively free of positive symptoms or it may be used in combination with known neuroleptics. A pharmaceutical composition containing both an $H_2$-antagonist and a neuroleptic is part of the present invention.

7 Claims, No Drawings

METHOD AND PHARMACEUTICAL COMPOSITION FOR THE TREATMENT OF SCHIZOPHRENIA

This application is a division of application Ser. No. 07/655,759, filed on Feb. 14, 1991, now U.S. Pat. No. 5,070,101.

BACKGROUND OF THE INVENTION

This application relates to a method and a pharmaceutical composition for the treatment of schizophrenia.

Schizophrenia is a chronic disabling disease which may occur in nearly 1% of the population worldwide. While there remains some dispute as to the proper diagnostic criteria for schizophrenia, it is generally accepted that schizophrenia manifests itself in two distinct sets of symptoms, referred to as positive and negative symptoms. See, e.g. Carpenter et al., Am. J. Psychiatry 145: 578-583 (1988); Morrison et al., J. Nervous and Mental Disease 178: 377-384 (1990).

The so-called positive symptoms of schizophrenia are typified by delusions, hallucinations and formal thought disorder. These symptoms have proven responsive to treatments with antidopaminergic neuroleptic drugs such as haloperidol, chlorpromazine, thioridazine and others. In contrast, the negative symptoms, which are typified by alogia, anhedonia, asociality, apathy, avolition, and amotivation have not been responsive to drug treatments. Because of this, and the fact that negative symptoms once developed tend to persevere, some authors have characterized this condition is "irreversible." Carpenter, supra at 579. Surprisingly, therefore, a drug therapy which is effective to treat the negative symptoms of schizophrenia has now been found.

SUMMARY OF THE INVENTION

In accordance with the present invention, persons suffering from negative symptoms of schizophrenia can be successfully treated using a histamine $H_2$-antagonist which crosses the blood-brain barrier so as to interact with histamine-$H_2$ receptors in the brain. A preferred $H_2$-antagonist is famotidine. The $H_2$-antagonist may be used alone in patients who are relatively free of positive symptoms or it may be used in combination with known neuroleptics. A pharmaceutical composition containing both an $H_2$-antagonist and a neuroleptic is part of the present invention.

DETAILED DESCRIPTION OF THE INVENTION

The discovery that histamine $H_2$-antagonists can be used to treat negative symptoms of schizophrenia was made during treatment of a 36 year old man with a 15 year history of schizophrenia and, coincidentally, peptic ulcers. The patient had been admitted to a hospital because of his schizophrenia two months prior to the discovery. At this time, he was found to have formal thought disorder, paranoid ideation, social withdrawal, psychomotor retardation, and emotional blunting. In the 5 years before admission he lived alone in a dark room in his parents' house, avoiding contact with others. He was not under the care of a psychiatrist, nor was he taking any medication.

On the inpatient unit he was put on haloperidol and benztropine. His thought disorder and paranoid symptoms resolved in 3 weeks; however, severe extrapyramidal symptoms developed which were only marginally responsive to increased benztropine. Neuroleptic treatment had to be suspended and the patient was put on medication-free observation. His negative symptoms of schizophrenia remained unchanged. A medical work-up during this time revealed symptomatic peptic ulcer disease. The patient was started on famotidine 40 mg daily 3 weeks after he stopped taking psychotropic medications. The negative symptoms improved 10 days after initiation of famotidine. The patient became more sociable, verbal, and active, and within 2 months he could take part in a rehabilitation work program. He was discharged on famotidine only with close follow-up.

The patient did very well, attending a work program daily and forming a relationship with a woman. Six months after discharge, when the patient was free of peptic ulcer symptoms, famotidine was discontinued by an internist—but within a month the patient became increasingly isolated, withdrawn, and guarded. He was readmitted and found to have severe negative symptoms with possible paranoid ideation. Since his peptic ulcer was again symptomatic and since his psychiatric symptoms had previously improved when famotidine had been prescribed, this drug was reintroduced. Within a week the patient was much improved mentally. Within 4 weeks he was back on the work program. He was discharged 2 weeks later in good condition on famotidine.

The remarkable success with this initial patient led to two avenues of follow-up efforts. First, efforts were undertaken to confirm the observed results in further patients. Secondly, a literature study was instituted to see if a mechanistic explanation for the observation could be found. Based on these two efforts, it now appears clear that histamine $H_2$-antagonists such as famotidine can be expected to have a beneficial effect on negative symptoms of schizophrenia in many patients.

A. Clinical Follow-Up Work

The initial observation that famotidine could be used to treat negative symptoms of schizophrenia was followed up with a more rigorous study which has involved four patients to date. Before being selected as a candidate for this study, subjects were tested using the SADS (Schedule for Affective Disorders and Schizophrenia); Simpson-Angus Neurological Rating Scale to assess extrapyramidal symptoms and RDC (Research Diagnostic Criteria) protocols. Those subjects scored as schizophrenic by the RDC were included, provided they did not meet the criteria for depression and provided that they had no marked prior history of alcohol or drug abuse, were physically healthy and did not require chronic medication (e.g., insulin). Suitable candidates were then tested using a preliminary SANS (Scale for Assessment of Negative Symptoms) to determine if negative symptoms are predominant.

The selected patients were each stabilized for at least one month prior to beginning famotidine treatment by administration of 0.2 mg/kg/day of haloperidol (Haldol) Prolyxin and then began receiving famotidine, together with the same dosage of antipsychotic, at a level of 40 mg/day. The four patients tested showed a marked reduction in negative symptoms and during the six weeks of the test. The improvement was primarily manifested by more animated behavior, increased activity, increased participation in occupational therapy, spontaneity, greater motivation and brighter affect.

Attention to personal grooming, hygiene and living environment also increased.

As a result of these observations, treatment with histamine H$_2$-antagonists such as famotidine offers promise for the treatment of many heretofore untreatable individuals. In particular, such treatment would appear to be indicated for patients diagnosed as schizophrenic with prominent negative symptoms, i.e., amotivation, anhedonia, lack of spontaneity, blunted affect, decreased ability to function, decreased ability to take care of oneself, decreased ability to relate to others and feelings of emptiness regardless of sex or age.

B. Mechanistic Considerations

Famotidine is a potent, highly selective H$_2$-receptor antagonist. Langtry, Drugs 38, 551-90 (1989). It has negligible activity at muscarinic, nicotinic, adrenergic, or H$_1$ receptors. Orally administered famotidine penetrates the blood/brain barrier and produces a CSF/plasma concentration ratio similar to that of cimetidine and ranitidine. Kagevi, Br. J. Clin. Pharmacol. 24, 849-50 (1987). These facts support the conclusion that famotidine is active against schizophrenia by acting as a histamine H$_2$-antagonist. We therefore investigated what was known about histamine and its relationship, if any, to schizophrenia.

Histamine serves as a neurotransmitter and neuromodulator in the brain, Prell, Ann. Rev. Neurosci 9, 209-54 (1986), and histaminergic receptors provide widespread innervation of neocortex, limbic structures, hypothalamus, and mesencephalon, with very high levels of H$_2$ activity in brain regions implicated in schizophrenia. Hough, progr. Neurobiol. 30, 469-505 (1988). H$_2$-receptors transmit primarily inhibitory signals; when stimulated, spontaneous activity and exploratory behavior decrease in animals. White et al., Psychopharmacol 95, 1-14 (1988). Thus, overactive H$_2$-receptor activity could, theoretically, contribute to the negative symptoms of schizophrenia. This possibility has not, however, been previously suggested as a mechanism for schizophrenia.

In fact, published literature on schizophrenia which mentions histamine suggests that low levels of histamine are responsible for schizophrenic symptoms and histamine itself was tested as a therapeutic agent. Heleniak et al., Medical Hypothesis 30, 167-174 (1989), Heleniak et al., J. Orthomolecular Psychiatry 14, 162-177. Further, schizophrenia-like psychosis was reported to have occurred following an overdose of an H$_2$-antagonist, Mandrox, Roman, Br. J. Psychiatry 121, 618-620 (1972). Nevertheless, this theory does fit with the apparently histamine-related phenomena observed in schizophrenic patients.

For example, it has been reported anecdotally that schizophrenic patients have a diminished sensitivity to pain. Such an effect could result from histamine overactivity in the central nervous system either due to high histamine levels in the brain or due to H$_2$ receptor hyperactivity and is reported to be blocked by H$_2$-antagonists.

Similarly, it has been observed that schizophrenic patients are prone to excessive water intake and water intoxication, particularly in chronic deteriorated patients. Since histamine is involved in the hypothalamus in regulation of eating and drinking, increased histamine receptor activity could be the cause of this condition.

Given these mechanistic considerations, it appears reasonable that other H$_2$-antagonists besides famotidine will be useful in the treatment of schizophrenia. Suitable H$_2$-antagonists include well known compounds such as cimetidine, ranetidine and nizatidine and newer H$_2$-blockers such as omeprazole, tiotidine, aminofurazan compounds and ORF 17578 (J. Pharmacol. Exp. Ther 237, 404-10(1986)).

As noted above, famotidine is effective when administered orally at levels of 40 mg/day. Thus dosages of from about 20 to about 80 mg/day are reasonable therapeutic levels. Other H$_2$-antagonists may require higher or lower dosage levels depending on the efficacy of the compound as an H$_2$-antagonist and the efficiency with which it crosses the blood/brain barrier. The determination of useful concentrations in such cases is a matter of routine. Similarly, if administration routes other than oral are desired, e.g., intravenous, or intramuscular, some adjustment in the daily dosage may be necessary based on bioavailability, but this is again a routine matter.

The preferred mode of administration is oral, as this is the most readily used in an outpatient setting. The H$_2$-antagonist is thus desirably packaged in dosage unit form as tablets or capsules. Further, the H$_2$-antagonist may be combined in a single composition with a maintenance dose of a neuroleptic such as haloperidol or prolyxin.

I claim:

1. A method of treating schizophrenia comprising administering to a patient exhibiting negative symptoms of schizophrenia a therapeutically effective amount of a histamine H$_2$-antagonist that crosses the blood/brain barrier and a neuroleptic drug effective to treat positive symptoms of schizophrenia, whereby both the positive and negative symptoms of schizophrenia are ameliorated.

2. A method according to claim 1, wherein the histamine H$_2$-antagonist is famotidine.

3. A method according to claim 2, wherein the famotidine is administered orally in an amount of from 20 to 80 mg per day.

4. A method according to claim 1, wherein the neuroleptic drug is haloperidol.

5. A pharmaceutical composition for the treatment of schizophrenia comprising
   (a) a histamine H$_2$-antagonist that crosses the blood/brain barrier and is effective to ameliorate negative symptoms of schizophrenia;
   (b) a neuroleptic drug effective to treat positive symptoms of schizophrenia; and
   (c) a pharmaceutically acceptable carrier.

6. A pharmaceutical composition according to claim 5, wherein the histamine H$_2$-antagonist is famotidine.

7. A pharmaceutical composition according to claim 6, wherein the neuroleptic drug is haloperidol.

* * * * *